(12) United States Patent
Blazevich

(10) Patent No.: US 11,826,281 B1
(45) Date of Patent: Nov. 28, 2023

(54) EYE DROP DISPENSER

(71) Applicant: John Z. Blazevich, Palos Verdes Peninsula, CA (US)

(72) Inventor: John Z. Blazevich, Palos Verdes Peninsula, CA (US)

( * ) Notice: Subject to any disclaimer, the term of this patent is extended or adjusted under 35 U.S.C. 154(b) by 0 days.

(21) Appl. No.: 18/186,090

(22) Filed: Mar. 17, 2023

(51) Int. Cl.
*A61F 9/00* (2006.01)
*B65D 47/18* (2006.01)

(52) U.S. Cl.
CPC ............ *A61F 9/0026* (2013.01); *B65D 47/18* (2013.01)

(58) Field of Classification Search
CPC ........ A61F 9/0008; A61F 9/00; A61F 9/0026; A61H 35/02; A61L 12/086; B65D 1/08; A61M 5/3202; A61M 5/001; A61M 5/158; A61M 5/3287; A61M 39/0208; A61M 39/0247; A61M 5/3134; A61M 2005/1587; A61M 2039/027; A61M 2039/0276; A61M 2039/0285; A61M 2039/0288; A61M 2039/0294; A61J 1/1406; A61J 1/2048; A61J 1/201; A61J 1/2055; A61J 1/2065; A61J 1/2096
See application file for complete search history.

(56) References Cited

U.S. PATENT DOCUMENTS

| | | | |
|---|---|---|---|
| 2,209,192 A * | 7/1940 | Demsey | A61F 9/0026 222/545 |
| 4,805,750 A | 2/1989 | Nitz | |
| 4,909,801 A | 3/1990 | Casey et al. | |
| 6,508,793 B1 | 1/2003 | Harrold | |
| D628,490 S | 12/2010 | Sato et al. | |
| 8,216,195 B2 | 7/2012 | Wu | |
| 9,763,826 B2 | 9/2017 | Cooper | |
| 2004/0007556 A1 * | 1/2004 | Manera | B65D 41/06 215/222 |
| 2007/0045354 A1 | 3/2007 | Boyd et al. | |
| 2013/0220967 A1 * | 8/2013 | Wang | B65D 47/0838 215/253 |

FOREIGN PATENT DOCUMENTS

JP   2019217056 A   * 12/2019

* cited by examiner

*Primary Examiner* — Nicholas J. Weiss
*Assistant Examiner* — Brandon W. Levy
(74) *Attorney, Agent, or Firm* — Knobbe, Martens, Olson & Bear, LLP

(57) ABSTRACT

An eye drop or eye wash dispenser assembly includes a dispenser bottle having a nipple for dispensing eye drops, and a cap removably coupleable to the dispenser bottle over the nipple. An eye cup removably fits over at least a portion of the dispenser bottle and couples to the bottle. The eye cup has a first open end with an oval shape and a second open end with a circular shape that is opposite the first open end. The eye cup can be coupled to the dispenser bottle in a stowed position where the eye cup is disposed below the nipple, and can be inverted and coupled to the dispenser bottle in a deployed position where the eye cup is disposed so that it extends distally of and around the nipple. The eye cup in the deployed position can be supported on or rest on the periphery of the eye socket to facilitate delivery of eye drops into a user's eye.

20 Claims, 7 Drawing Sheets

EYE DROP DISPENSER

BACKGROUND

Field

The present disclosure is directed to an eye drop or eye wash dispenser, and more particularly to an eye drop or eye wash dispenser with an eye cup for dispensing eye drops or eye wash.

Description of the Related Art

Eye drops are regularly used to treat eye conditions such as dry eye, bacterial infections, eye injury or eye conditions such as glaucoma and cataracts. Existing eye drop dispensers are deficient in that they do not accurately or consistently deliver the drops into the eye (e.g., affecting children and elderly people more), often delivering the drops on other parts of the user's face, leading to multiple attempts and making the process difficult to administer. Also, there is an unnecessary wasting of the eye drops, thereby costing the consumer more. Additionally, it can be even more difficult to deliver eye drops with exiting dispensers when the user suffers from hand tremors so that their hands shake while trying to deliver the eye drops, such as individuals suffering from essential tremor disorder or other neurological conditions. Such difficulty in delivering eye drops with existing dispenser designs can lead to a decrease in compliance by users to take the medication.

SUMMARY

In some aspects, the techniques described herein relate to an eye drop dispenser assembly, including: a dispenser bottle having a nipple via which eye drops are dispensed and a coupling mechanism proximate the nipple; a cap removably coupleable to the dispenser bottle over the nipple; and an eye cup having a first open end and a second open end opposite the first open end and configured to removably fit over at least a portion of the dispenser bottle, the first open end having an oval shape and the second open end having a circular shape, the eye cup being coupleable to the coupling mechanism of the dispenser bottle in a stowed position where the eye cup is disposed below the nipple and an outer surface of the eye cup aligns with an outer surface of a lower portion of the dispenser bottle, the eye cup further being coupleable to the coupling mechanism of the dispenser bottle in a deployed position where the eye cup is disposed so that it extends around and distally from the nipple, wherein the eye cup in the deployed position facilitates delivery of eye drops into a user's eye.

In some aspects, the techniques described herein relate to an eye drop dispenser assembly, including: a dispenser bottle having a nipple via which eye drops are dispensed; a cap removably coupleable to the dispenser bottle over the nipple; and an eye cup having a first open end and a second open end opposite the first open end and configured to removably fit over at least a portion of the dispenser bottle, the first open end having an oval shape and the second open end having a circular shape, the eye cup being coupleable to the dispenser bottle in a stowed position where the eye cup is disposed below the nipple, the eye cup further being coupleable to the dispenser bottle in a deployed position where the eye cup is inverted and disposed so that it extends around and distally of the nipple, wherein the eye cup in the deployed position is configured to be disposed proximate an eye socket of a user's eye and facilitates delivery of eye drops into a user's eye.

In some aspects, the techniques described herein relate to a method for dispensing eye drops from an eye drop dispenser, including: decoupling an eye cup from a dispenser bottle, where the eye cup is in a stowed position and extends around an upper portion of the dispenser bottle, the eye cup having a first open end and a second open end opposite the first open end, the first open end having an oval shape and the second open end having a circular shape; inverting the eye cup; coupling and inverted eye cup to the dispenser bottle so that the eye cup extends distally of and around a nipple of the dispenser bottle and distal of the upper portion; aligning the first open end of the eye cup over an eye socket of a user; and dispensing one or more eye drops from the dispenser bottle into an eye of the user.

DETAILED DESCRIPTION

Figure 1:
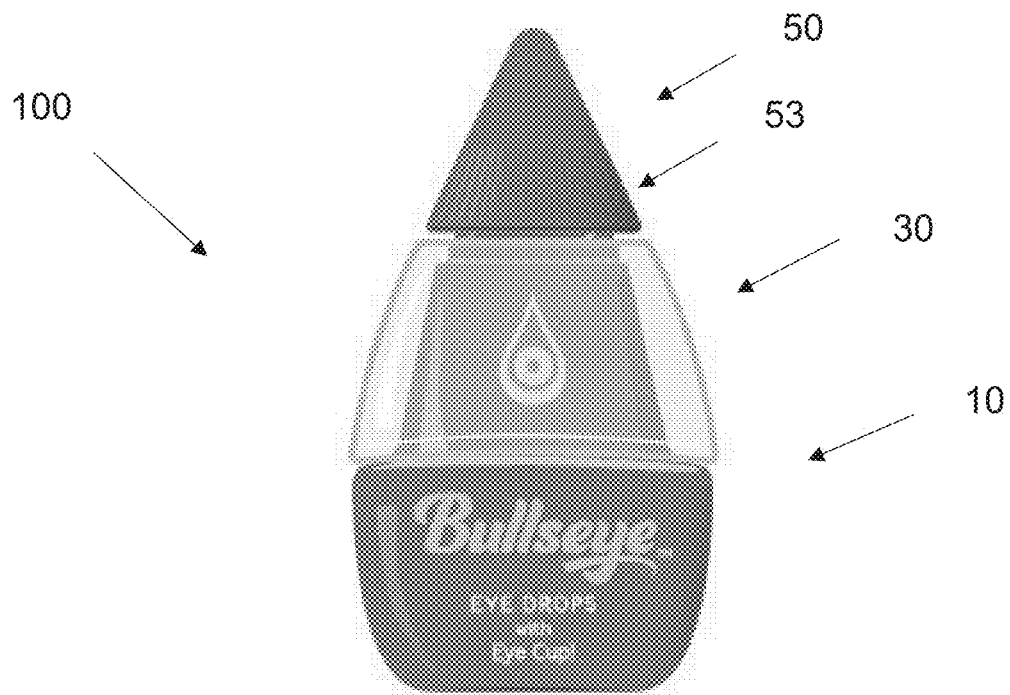
FIG. 1 is a schematic front view of an eye drop dispenser assembly.

FIGS. 1-8 show an eye drop dispenser assembly 100 (the "assembly 100"). The assembly 100 includes a dispenser bottle 10, an eye cup 30 and a cap 50. FIG. 1 shows the assembly 100 assembled with the eye cup 30 in the stowed position so that the assembly 100 is generally shaped like a water droplet or tear drop. However, the eye drop dispenser assembly can have other shapes, as discussed further below in connection with FIGS. 9 and 10. The cap 50 can be a single piece (e.g., monolithic, seamless) with a sidewall 53. The dispenser bottle 10, the eye cup 30 and/or the cap 50 can optionally be made in part or whole of plastic, silicone or rubber. However, the dispenser 10, the eye cup 40 and/or the cap 50 can be made of other suitable materials (e.g., flexible or resilient materials). The cap 50 is removably coupleable to the dispenser bottle 10 and can optionally have a conical shape.

Figure 2:
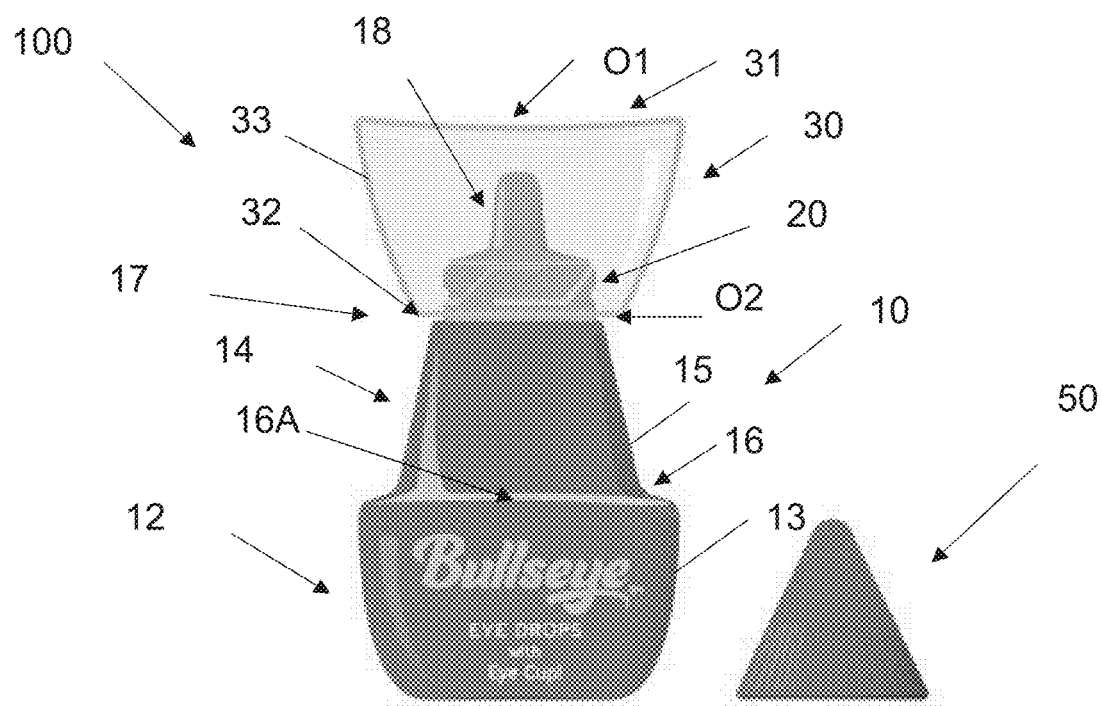
FIG. 2 is a schematic front view of the eye drop dispenser of FIG. 1 with its cap removed and the eye cup in a deployed position extending around a nipple of the dispenser bottle.
Figures 3A, 3B:
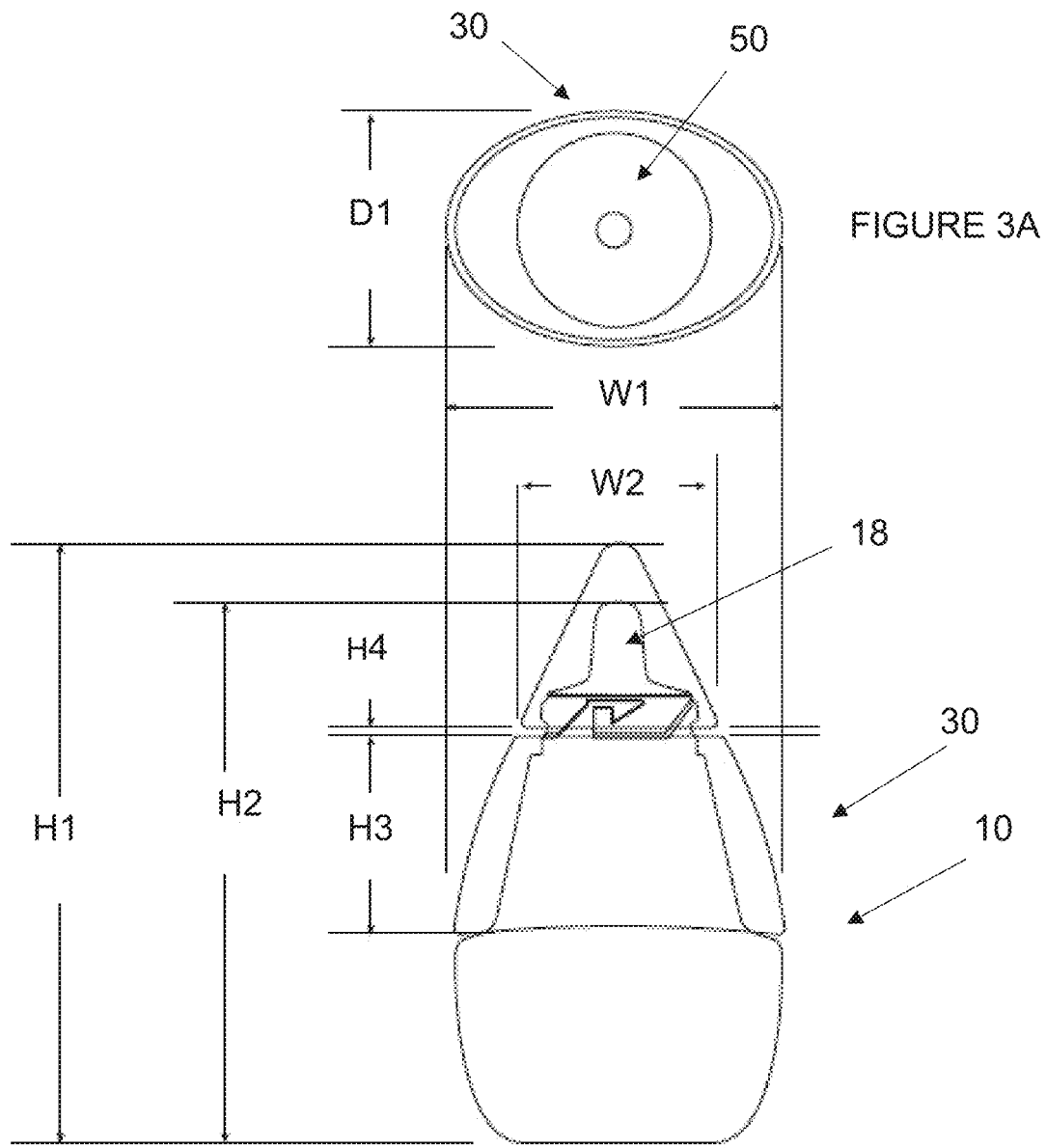
FIG. 3A is a schematic top view of the eye drop dispenser assembly of FIG. 1.
FIG. 3B is a schematic side view of the eye drop dispenser assembly of FIG. 1.
Figure 4:
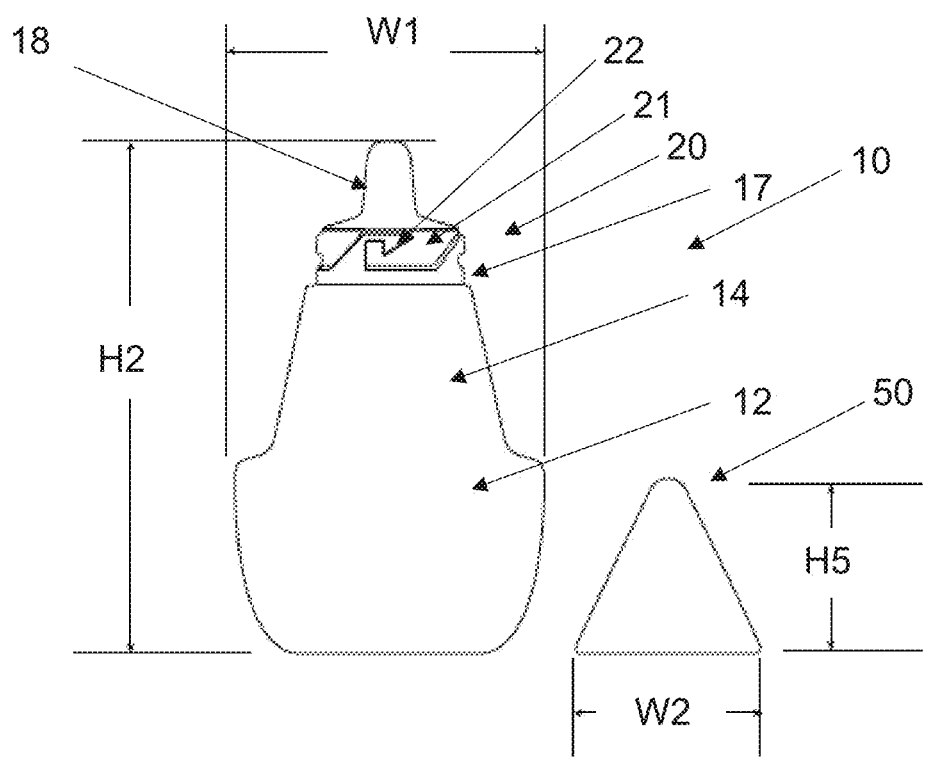
FIG. 4 is a schematic side view of the dispenser bottle for the eye drop dispenser assembly of FIG. 1 with its cap removed and to the side.
Figure 5:
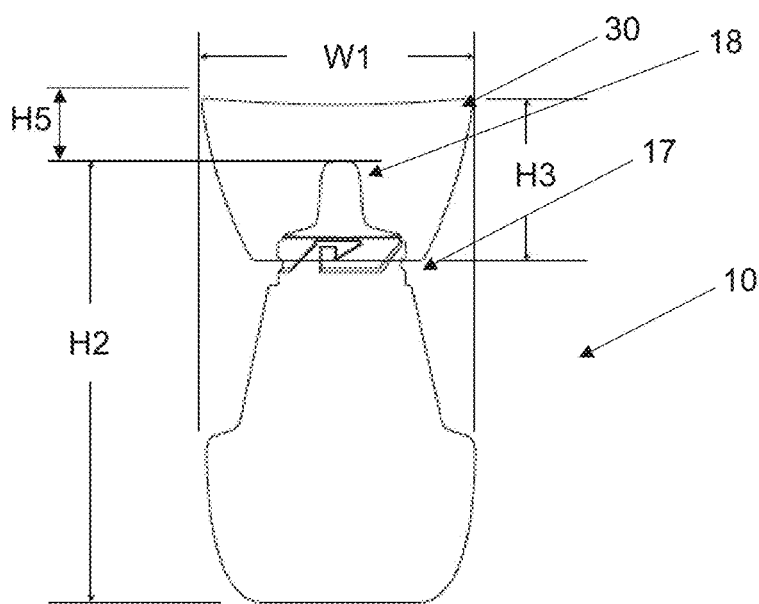
FIG. 5 is a schematic front view of the eye drop dispenser of FIG. 1 with its cap removed and the eye cup in a deployed position extending around the nipple of the dispenser bottle.

The dispenser bottle 10 has a chamber (not shown) that can hold a liquid (e.g., eye drop formulation, liquid medication). In one example, the eye drops dispensed by the eye drop dispenser assembly 100 can be eye lubricant drops. The liquid can be a formulation for treating a condition of the eyes (e.g., dry eye, bacterial infections, cataracts, glaucoma, or for treating eye injuries). The dispenser bottle 10 can optionally be made of plastic, silicone, rubber, or other suitable resilient or flexible material. The dispenser bottle 10 is a single piece (e.g., a monolithic, seamless single piece). The dispenser bottle 10 can optionally include a lower portion 12 with a sidewall 13 and an upper portion 14 with a sidewall 15, the dispenser bottle 10 having a shoulder 16 (e.g., lower shoulder) between the upper portion 14 and the lower portion 12. In some implementations, the lower portion 12 can be cylindrical. The shoulder 16 can have a curved or contoured edge 16A on the front, side and rear of the dispenser bottle 10. In one implementation, the sidewall 13 is curved or contoured. In one implementation, the sidewall 15 is generally linear and tapers between the shoulder 16 and a second shoulder 17 (e.g., upper shoulder 17), as shown in FIGS. 2 and 4. That is, the lower portion 12 has a larger width than the upper portion 14. The dispenser bottle 10 includes a nipple 18 at an end of the dispenser bottle 10 that is opposite the lower portion 12. The dispenser bottle 10 includes a locking mechanism 20 disposed between the second shoulder 17 and the nipple 18. In one example, the locking mechanism 20 includes one or more recesses 21 (e.g., multiple recesses, two recesses, four recesses) and one or more hooks 22 (e.g., multiple hooks, two hooks, four hooks), as shown in FIGS. 4-5. The locking mechanism 20 can additionally or alternatively include one or more threads for threadably coupling with the cap 50 and/or the eye cup 30. Other suitable locking mechanisms can be used. For example, the locking mechanism can be a clip-on mechanism (e.g., that allows the eye cup 30 to clip onto the bottle dispenser 10, such as via multiple clips that clip into depressions in the bottle dispenser), or a press-fit mechanism, where the eye cup 30 is press-fit (e.g., friction fit) onto the dispenser bottle 10. In another example, the locking mechanism can be a threaded coupling, where the eye cup 30 is threadably coupled to threads on the dispenser bottle 10.

The eye cup 30, see FIG. 2, can have a first edge 31 (e.g., bottom edge), a second edge 32 (e.g., top edge) opposite the first edge 31, and a sidewall 33 that extends between and interconnects the first edge 31 and the second edge 32. The eye cup 30 can optionally be transparent. The eye cup 30 can optionally be made of plastic, silicone, rubber or other suitable resilient or flexible material. The eye cup 30 can be a single piece (e.g., a monolithic, seamless single piece). In other embodiments the eye cup 30 can be multiple pieces that can be assembled together. The eye cup 30 can be hollow with the first edge 31 defining a first opening O1 and the second edge 32 defining a second opening O2 opposite the first opening O1. The eye cup 30 is removably coupleable to the dispenser bottle 10. The eye cup 30 can have one or more protrusions or tabs 34 (e.g., multiple, two, four spaced apart protrusions) that extend radially inward from the second edge 32 into the second opening O2 (see FIGS. 7-7A). The first opening O1 and first edge 31 can have a larger perimeter than the second opening O2 and second edge 32, the sidewall 33 tapering between the first edge 31 and the second edge 32 (e.g., tapering in a curved manner).

Figure 8:
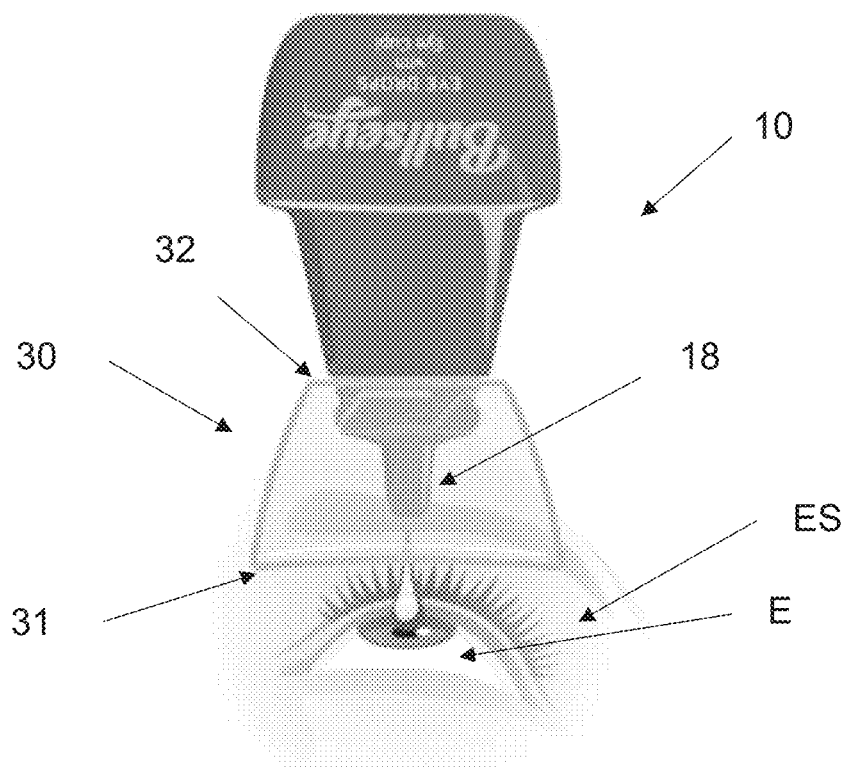
FIG. 8 is a schematic view of the eye drop dispenser of FIG. 2 in an upside down position over a user's eye to deliver an eye drop thereto.

As best shown in FIG. 8, the first edge 31 (and first opening O1) can have an oval shape and the second edge 32 (and second opening O2) can have a circular shape. With continued reference to FIG. 2, the first edge 31 can be curved. In one implementation, the first edge 31 is curved or contoured and generally corresponds with a curvature of the contoured edge 16A of the shoulder 16. The second edge 31 can be linear.

With continued reference to FIG. 1, when the eye cup 30 is in the stowed position on the dispenser bottle 10, the eye cup 30 extends around the upper portion 14 (see FIG. 2) of the dispenser bottle 10 (and completely below the nipple 18), and the protrusions 34 (see FIG. 7) are coupled to the locking mechanism 20 (e.g., the protrusions 34 extend within the recesses 21 and couple to the hooks 22 of the locking mechanism 20) to maintain the eye cup 30 coupled to the dispenser bottle 10 (e.g., even if the cap 50 is removed and the dispenser bottle 10 turned upside down). In the stowed position (shown in FIG. 1), the sidewall 33 of the eye cup 30 aligns (e.g., defines a generally continuous edge) with the sidewall 13 of the lower portion 12 of the dispenser bottle 10, and the sidewall 33 also generally aligns with the sidewall 53 of the cap 50, advantageously providing a compact assembly when the eye cup 30 is in the stowed position over the dispenser bottle 10.

With continued reference to FIG. 2, when the eye cup 30 is in the deployed position on the dispenser bottle 10, the eye cup 30 extends around the nipple 18 (and completely above the upper portion 14 of the dispenser bottle 10). In the deployed position, the eye cup 30 is oriented so that the second edge 32 is adjacent the shoulder 17, the protrusions 34 are coupled to the locking mechanism 20 (as described above), and the first edge 31 and first opening O1 are disposed above the nipple 18 (e.g., so that the first edge 31 defines a topmost end of the assembly 100).

FIGS. 3A-5 show schematic views of the eye drop dispenser assembly 100 with the eye cup 30 in the stowed position (FIGS. 3A-3B), with the cap 50 removed and excluding the eye cup 30 (FIG. 4) and with the cap 50 removed and the eye cup 30 in the deployed position (FIG. 5). The assembly 100 has a height H1 between a base of the bottle dispenser 10 and a top of the cap 50, and a height H2 between the base of the bottle dispenser 10 and the end of the nipple 18. In one implementation, the height H1 is between about 2.5 and 3.5 inches, such as 3 inches, and the height H2 is between about 2.3 and about 3.4 inches, such as 2.9 inches. The eye cup 30 has a height H3 of between about 0.75 inches and about 1.3 inches, such as 1 inch, a width W1 of between about 1.3 inches and 2.3 inches, such as 1.8 inches, and a depth D1 of between about 1 inch and about 1.5 inches, such as 1¼ inches. The cap 50 can have a width W2 of between about 0.75 inches and about 1.25 inches, such as about 1 inch, and a height H5 of between about 0.75 inches and about 1.25 inches, such as about 1 inch. With reference to FIG. 3B, a gap H4 between the second edge 32 of the eye cup 30 and the bottom of the cap 50 can be between about 0.005 inches and about 0.07 inches, such as about 0.05 inches. When in the deployed or inverted position, the eye cup 30 can extend a height H5 past the nipple 18. In one example, the height H5 is between about 0.1 inches and about 0.5 inches, such as about ¼ inch and facilitates a soft landing of the eye drop onto the eye. The height H5 can also help ensure the eye drop is delivered into the eye and does not run off the eye (e.g., onto the user's face, such as cheek).

Figure 6:
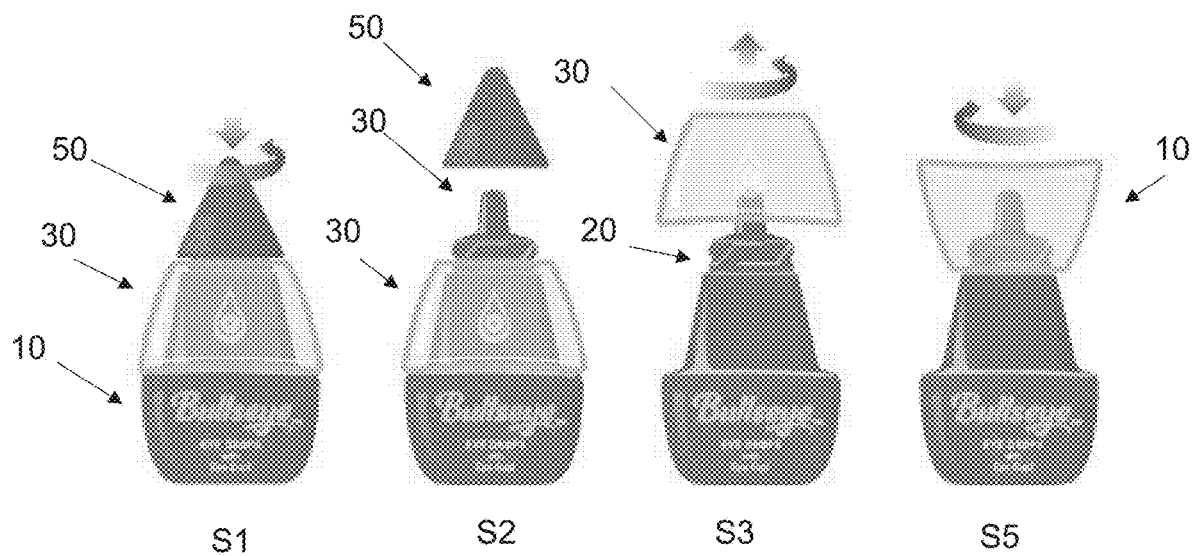
FIG. 6 shows side views of the eye drop dispenser assembly of FIG. 1, showing process steps for using the eye drop dispenser assembly.
Figure 7:
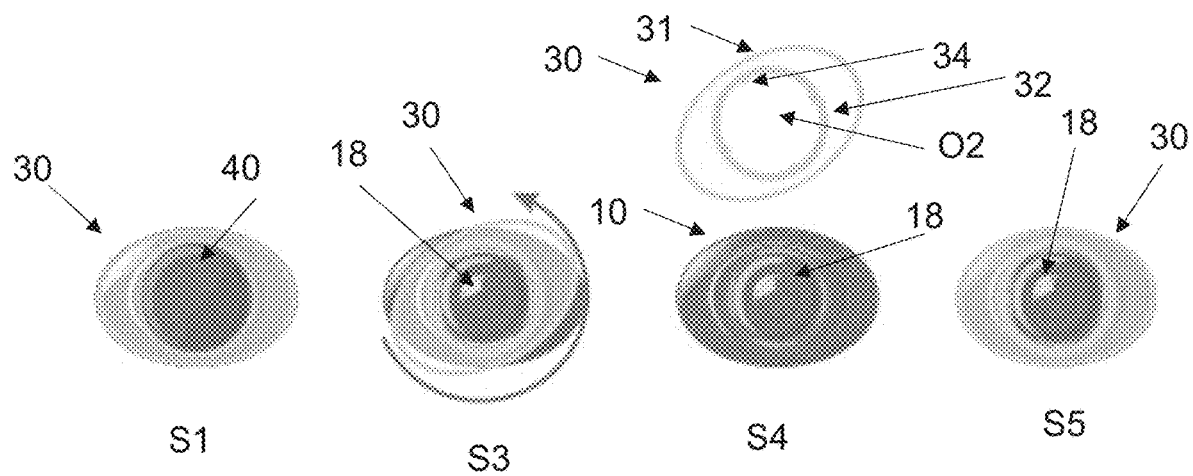
FIG. 7 shows top views of the eye drop dispenser assembly of FIG. 1, showing process steps for using the eye drop dispenser assembly.
Figure 7A:
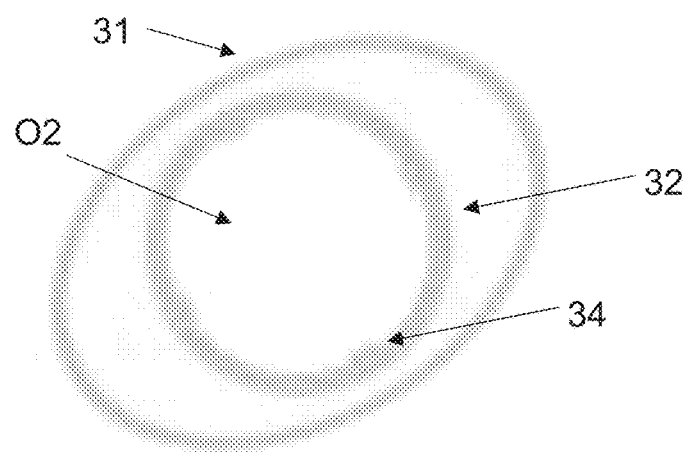
FIG. 7A is an enlarged end view of the eye cup of the eye drop dispenser assembly.

FIG. 6-8 show process steps for using the eye drop dispenser assembly 100 to dispense eye drops. At step S1, the eye drop dispenser assembly 100 is in the assembled state with the eye cup 30 in the stowed position on the dispenser bottle 10 (e.g., coupled to the dispenser bottle 10) and the cap 50 disposed over the nipple 18. At step S2, the cap 50 is removed to expose the nipple 18. At step S3, the eye cup 30 is decoupled from the dispenser bottle 10, for example by rotating the eye cup 30 relative to the dispenser bottle 10 allowing the protrusions 34 to disengage the hooks 22 and exit the recesses 21 (see FIG. 4) of the locking mechanism 20. At step S4 (see FIG. 7), the eye cup 30 is completely removed from over the dispenser bottle 10 and is then inverted. At step S5 (see FIG. 6), the inverted eye cup 30 is coupled to the dispenser bottle 10 by advancing the eye cup 30 so the second opening O2 is past the nipple 18 and so the protrusions 34 extend into the recesses 21 and engage the hooks 22 of the locking mechanism 20 to couple (e.g., lock) the inverted eye cup 30 to the dispenser bottle 10.

As shown in FIG. 8, the assembly 100 can be inverted and disposed over an eye E so that the inverted eye cup 30 is disposed over (e.g., in contact with) an eye socket ES of the eye E. The user can then squeeze the dispenser bottle 10 to dispense one or more drops into the eye E. Advantageously, the eye cup 30 is sized so that the first edge 31 can be disposed over (e.g., in contact with) an eye socket ES of an eye E so that the first opening O1 is aligned with the eye, the contoured first edge 31 of the eye cup 30 advantageously allowing the eye cup 30 to comfortably sit or rest over the eye socket ES, thereby facilitating alignment of the nipple 18 with the eye E and facilitating the dispensing of the eye drop(s) directly into the eye, thereby inhibiting (e.g., preventing) waste from having the eye drops fall on the user's face, cheek or eye brow, etc. The ability of the eye cup 30 to sit or rest over the eye socket ES (e.g., sit or rest on a periphery of the eye socket ES) can advantageously facilitate use of the eye drop dispenser assembly 100 by a user with hand tremors, nervous disorders or children to dispense eye drops into the eye. Additionally, supporting (e.g., sitting or resting) the eye cup 30 over the eye socket ES can inhibit (e.g., prevent) injury to the eye during delivery of eye drops.

Figure 9:
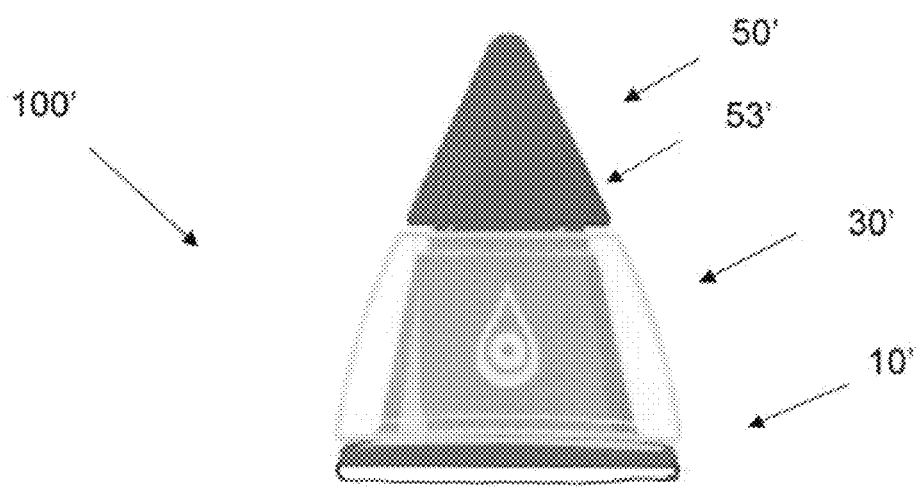
FIG. 9 is a schematic front view of an eye drop dispenser assembly.

FIG. 9 shows a schematic view of an eye drop dispenser assembly 100' (hereafter "the assembly 100'"), which is a compact version of the eye drop dispenser assembly 100. Some of the features of the assembly 100' are similar to features of the assembly 100 in FIGS. 1-8. Thus, reference numerals used to designate the various components of the assembly 100' are identical to those used for identifying the corresponding components of the assembly 100 in FIGS. 1-8, except that a "'" has been added to the numerical identifier. Therefore, the structure and description for the various features of the assembly 100 and how it's operated and controlled in FIGS. 1-8 are understood to also apply to the corresponding features of the assembly 100' in FIG. 9, except as described below.

The assembly 100' differs from the assembly 100 in that its shape resembles a pyramid. In one example, the dispenser bottle 10' is shorter than the dispenser bottle 10, holds a smaller liquid volume, and has a base that supports the eye cup 30' thereon in the stowed position. In other implementation, the dispenser bottle 10' can have a cylindrical portion below the eye cup 30'.

Figure 10:
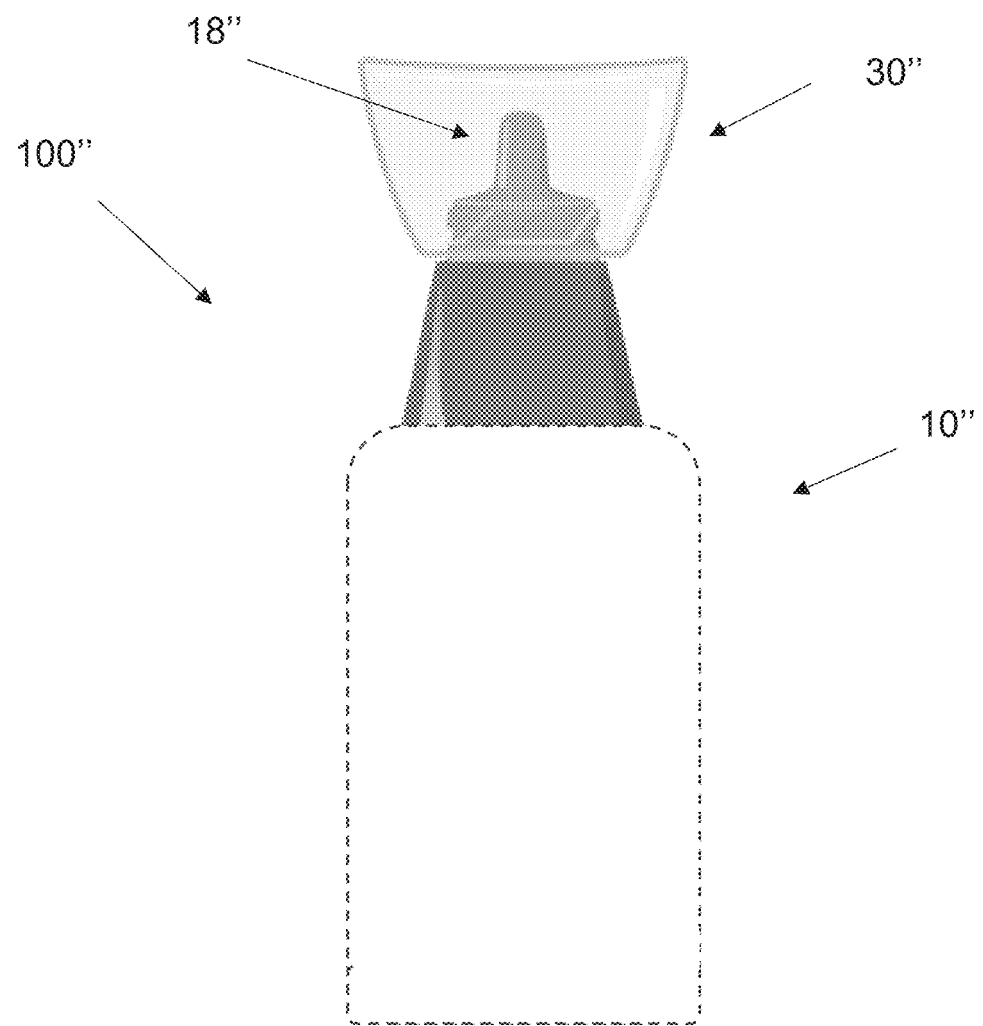
FIG. 10 is a schematic front view of an eye wash dispenser assembly.

FIG. 10 shows a schematic view of an eye wash dispenser assembly 100" (hereafter "the assembly 100'"), which is an eye wash version of the eye drop dispenser assembly 100. Some of the features of the assembly 100" are similar to features of the assembly 100 in FIGS. 1-8. Thus, reference numerals used to designate the various components of the assembly 100" are identical to those used for identifying the corresponding components of the assembly 100 in FIGS. 1-8, except that a "'"" has been added to the numerical identifier. Therefore, the structure and description for the various features of the assembly 100 and how it's operated and controlled in FIGS. 1-8 are understood to also apply to the corresponding features of the assembly 100" in FIG. 10, except as described below.

The assembly 100" differs from the assembly 100 in that the dispenser bottle 10" is larger and holds a larger volume of solution. The dispenser bottle 10" can have any shape (e.g., cylindrical), as represented by the dashed lines in FIG. 10. The solution can be an eye wash or multipurpose solution (e.g., saline) that can be used to wash out an eye (e.g., following injury to the eye, exposure to a contaminant, such as a poisonous substance, or to treat irritation of the eye). The nipple 18" can differ from the nipple 18' in that it can have a larger opening to allow a stream of solution to be dispensed (e.g., continuously) from the dispenser bottle 10" into the eye.

The assembly 100, 100', 100" is advantageously easy to use (e.g., easy to remove the cap 50, easy to decouple and couple the eye cup 30, 30', 30" from the dispenser bottle 10, 10', 10"). Such ease of use of the eye drop dispenser assembly 100, 100' will result in increased compliance by users (e.g., senior citizens, children) to use the eye drops regularly or as recommended by a doctor, resulting in more people using it more often (e.g., as prescribed) and an increase in sales of the eye drop dispenser assembly 100, 100'. Additionally, the eye cup 30, 30', 30" advantageously allows a user who may have tremors or other neurological challenges to be able to deliver the eye drops themselves by supporting or resting the eye cup 30, 30', 30" over the eye socket ES (e.g., support or rest the eye cup 30, 30', 30" on the periphery of the eye socket ES) to ensure the eye drops are delivered into their eye E. The eye cup 30, 30', 30" is advantageously sized and shaped to conform to an eye socket ES (e.g., can be supported and/or rested against the user's eye socket ES) and facilitates alignment of the nipple 18, 18', 18" with the eye E when the eye cup 30, 30', 30" is disposed over (e.g., proximate, in contact with) the periphery of the eye socket ES to ensure delivery of eye drops or eye wash into the eye E. Supporting or resting the eye cup 30, 30', 30" over the eye socket ES (e.g., disposed over or in contact with the periphery of the eye socket ES) can inhibit (e.g., prevent) injury to the eye while attempting to administer eye drops or eye wash (e.g., into an active child or a neurologically compromised person). Further, the assembly 100, 100', 100" facilitates eye drop or eye wash use with children by ensuring the nipple 18, 18', 18" is aligned with the child's eye before dispensing the eye drops from the dispenser bottle 10, 10', 10". Further, as shown in FIG. 7, step S5, the eye cup 30 is disposed on the dispenser bottle 10 so that it extends around and distally of the nipple 18, and so that the eye cup 30 disposed relative to the nipple 18 resembles an eye. The nipple 18, 18', 18" (e.g., a tip of the nipple 18, 18', 18") can resemble a bullseye (e.g., be colored, such as with the color red), which can provide a focal point for the user to focus on (or to help distract the user, such as a child) while dispensing eye drops or eye wash. Additionally, the eye drop or eye wash dispenser assembly 100, 100', 100" advantageously provides a safe and sanitary (e.g., sterile) manner of delivering eye drops or eye wash (e.g., because the nipple 18, 18', 18" does not touch the user's eye. The assembly 100, 100', 100" is elegantly simple, intuitive and quick to use and provides a streamlined design.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A eye drop dispenser assembly, comprising:
   a dispenser bottle having a nipple via which eye drops are dispensed, a coupling mechanism proximate the nipple, and an upper portion recessed relative to a lower portion;
   a cap removably coupleable to the dispenser bottle over the nipple; and
   an eye cup having a first open end and a second open end opposite the first open end and configured to removably fit over at least a portion of the dispenser bottle, the first open end having an oval shape and the second open end having a circular shape, the eye cup being coupleable to the coupling mechanism of the dispenser bottle in a stowed position where the eye cup is disposed below the nipple and about the upper portion of the dispenser bottle so an outer surface of the eye cup circumferentially aligns with an outer surface of the lower portion of the dispenser bottle, the eye cup further being coupleable to the coupling mechanism of the dispenser bottle in a deployed position where the eye cup is disposed so that it extends around and distally from the nipple,
   wherein the eye cup in the deployed position facilitates delivery of eye drops into a user's eye.

2. The assembly of claim 1, wherein the coupling mechanism includes one or more recesses and one or more hooks.

3. The assembly of claim 2, wherein the eye cup has one or more protrusions that extend inward of the second open end, the one or more protrusions configured to extend into the one or more recesses and engage the one or more hooks to lock the eye cup to the dispenser bottle.

4. The assembly of claim 1, wherein the upper portion tapers from the lower portion toward the nipple.

5. The assembly of claim 1, further comprising a shoulder between the lower portion and the upper portion, the first open end of the eye cup configured to be disposed proximal to the shoulder when the eye cup is in the stowed position.

6. The assembly of claim 1, wherein an outer surface of the eye cup tapers between the first open end and the second open end.

7. The assembly of claim 1, wherein the eye cup has a curved edge at the first open end.

8. The assembly of claim 1, wherein when the eye cup is coupled to the dispenser bottle in the stowed position and the cap is disposed over the nipple, the eye drop dispenser assembly is shaped as a water droplet or tear drop when viewed from a front view.

9. A eye drop dispenser assembly, comprising:
   a dispenser bottle having a nipple via which eye drops are dispensed;
   a cap removably coupleable to the dispenser bottle over the nipple; and
   an eye cup having a first open end and a second open end opposite the first open end and configured to removably fit over at least a portion of the dispenser bottle, the first open end having an oval shape and the second open end having a circular shape, the eye cup being coupleable to the dispenser bottle in a stowed position where the first open end and the second open end of the eye cup are disposed below the nipple, the eye cup further being coupleable to the dispenser bottle in a deployed position where the eye cup is inverted and disposed so that it extends around and distally of the nipple,
   wherein the eye cup in the deployed position is configured to be disposed proximate an eye socket of a user's eye and facilitates delivery of eye drops into a user's eye.

10. The assembly of claim 9, wherein the eye cup has one or more protrusions configured to extend into one or more recesses of the dispenser bottle to couple the eye cup to the dispenser bottle.

11. The assembly of claim 9, wherein the dispenser bottle has an upper portion between a lower portion and the nipple, the lower portion having a greater width than the upper portion, the upper portion tapering from the lower portion toward the nipple.

12. The assembly of claim 11, further comprising a shoulder between the lower portion and the upper portion, the first open end of the eye cup configured to be disposed proximal to the shoulder when the eye cup is in the stowed position so that an outer surface of the eye cup aligns with an outer surface of the lower portion of the dispenser bottle.

13. The assembly of claim 9, wherein an outer surface of the eye cup tapers between the first open end and the second open end.

14. The assembly of claim 9, wherein the eye cup has a curved edge at the first open end.

15. A method for dispensing eye drops from an eye drop dispenser, comprising:
   decoupling an eye cup from a dispenser bottle, where the eye cup is in a stowed position and extends around an upper portion of the dispenser bottle, the eye cup having a first open end and a second open end opposite the first open end, the first open end having an oval shape and the second open end having a circular shape, where the first open end and the second open end of the eye cup are disposed below a nipple of the dispenser bottle when the eye cup is in the stowed position;
   inverting the eye cup;
   coupling an inverted eye cup to the dispenser bottle so that the eye cup extends distally of and around the nipple of the dispenser bottle and distal of the upper portion;
   aligning the first open end of the eye cup over an eye socket of a user; and
   dispensing one or more eye drops from the dispenser bottle into an eye of the user.

16. The method of claim 15, wherein decoupling the eye cup from the dispenser bottle includes rotating the eye cup relative to the dispenser bottle to unlock the eye cup from the dispenser bottle, and then linearly removing the eye cup from the dispenser bottle.

17. The method of claim 15, wherein coupling the eye cup to the dispenser bottle includes linearly advancing the eye cup relative to the dispenser bottle until the first open end is past the nipple and then rotating the eye cup relative to the dispenser bottle to lock the eye cup to the dispenser bottle.

18. The method of claim 15, wherein inverting the eye cup includes positioning the eye cup so that the second open end is closest to the upper portion of the dispenser bottle.

19. The method of claim 15, wherein aligning the eye cup over the eye socket includes supporting or resting the eye cup on a periphery of the eye socket.

20. The method of claim 15, wherein aligning the eye cup includes placing the eye cup relative to the eye socket so that a colored tip of the nipple resembles a bullseye the user can focus on during delivery of the one or more eye drops.

* * * * *